United States Patent
Roche et al.

(10) Patent No.: US 9,011,448 B2
(45) Date of Patent: Apr. 21, 2015

(54) ORTHOPEDIC NAVIGATION SYSTEM WITH SENSORIZED DEVICES

(75) Inventors: Martin Roche, Fort Lauderdale, FL (US); Marc Boillot, Plantation, FL (US); Jason McIntosh, Sugar Hill, GA (US)

(73) Assignee: Orthosensor Inc., Dania Beach, FL (US)

( * ) Notice: Subject to any disclaimer, the term of this patent is extended or adjusted under 35 U.S.C. 154(b) by 668 days.

(21) Appl. No.: 12/901,094

(22) Filed: Oct. 8, 2010

(65) Prior Publication Data

US 2011/0160583 A1    Jun. 30, 2011

Related U.S. Application Data

(60) Provisional application No. 61/291,725, filed on Dec. 31, 2009.

(51) Int. Cl.
 *A61F 2/46* (2006.01)
 *A61B 5/05* (2006.01)
 *A61B 19/00* (2006.01)

(52) U.S. Cl.
 CPC ..... *A61B 19/5244* (2013.01); *A61B 2019/5248* (2013.01); *A61B 2019/5263* (2013.01)

(58) Field of Classification Search
 USPC ........ 600/407, 437, 440–446, 448; 606/86 R, 606/87, 130
 See application file for complete search history.

(56) References Cited

U.S. PATENT DOCUMENTS

| | | | |
|---|---|---|---|
| 5,274,363 A | 12/1993 | Koved et al. | |
| 5,285,677 A * | 2/1994 | Oehler | 73/24.01 |
| 6,090,114 A | 7/2000 | Matsuno et al. | |
| 6,130,663 A | 10/2000 | Null | |
| 6,137,427 A | 10/2000 | Binstead | |
| 6,313,825 B1 | 11/2001 | Gilbert | |
| 6,490,467 B1 | 12/2002 | Bucholz et al. | |
| 6,508,403 B2 * | 1/2003 | Arsenault et al. | 235/454 |
| 6,546,277 B1 | 4/2003 | Franck et al. | |
| 6,859,661 B2 * | 2/2005 | Tuke | 600/424 |
| 6,925,339 B2 | 8/2005 | Grimm et al. | |
| 6,937,227 B2 | 8/2005 | Qamhiyah et al. | |
| 7,078,911 B2 | 7/2006 | Cehelnik | |
| 7,081,884 B2 | 7/2006 | Kong | |
| 7,092,109 B2 | 8/2006 | Satoh et al. | |
| 7,130,754 B2 | 10/2006 | Satoh et al. | |
| 7,139,418 B2 | 11/2006 | Abovitz et al. | |
| 7,141,020 B2 * | 11/2006 | Poland et al. | 600/447 |
| 7,309,339 B2 | 12/2007 | Cusick et al. | |
| 7,344,493 B2 * | 3/2008 | Sonnenschein et al. | 600/117 |
| 7,392,076 B2 | 6/2008 | Moctezuma de La Barrera | |
| 7,395,181 B2 | 7/2008 | Foxlin | |

(Continued)

FOREIGN PATENT DOCUMENTS

| | | |
|---|---|---|
| EP | 1372517 | 1/2004 |
| EP | 1444962 | 8/2004 |
| EP | 1570801 | 9/2005 |

*Primary Examiner* — Anu Ramana

(57) ABSTRACT

A low-cost and compact electronic device toolset is provided for orthopedic assisted navigation. The toolset comprises wireless sensorized devices that communicate directly with one another. A computer workstation is an optional component for further visualization. The sensorized devices are constructed with low-cost transducers and are self-powered. The toolset is disposable and incurs less hospital maintenance and overhead. As one example, the toolset reports anatomical alignment during a surgical workflow procedure. Other embodiments are disclosed.

12 Claims, 11 Drawing Sheets

(56) References Cited

U.S. PATENT DOCUMENTS

| | | |
|---|---|---|
| 7,477,926 B2 | 1/2009 | McCombs |
| 7,559,931 B2 | 7/2009 | Stone |
| 7,604,645 B2 | 10/2009 | Barzell et al. |
| 7,636,595 B2 | 12/2009 | Marquart et al. |
| 7,657,298 B2 | 2/2010 | Moctezuma de la Barrera et al. |
| 7,660,623 B2 | 2/2010 | Hunter et al. |
| 7,681,448 B1 | 3/2010 | Preston et al. |
| 7,685,861 B2 | 3/2010 | Lynch et al. |
| 7,689,032 B2 | 3/2010 | Strassenburg-Kleciak |
| 7,771,436 B2 | 8/2010 | Moctezuma De La Barrera et al. |
| 7,824,328 B2 | 11/2010 | Gattani et al. |
| 8,046,050 B2 | 10/2011 | Govari et al. |
| 8,057,479 B2 | 11/2011 | Stone |
| 8,068,648 B2 | 11/2011 | Disilvestro et al. |
| 2001/0011175 A1 | 8/2001 | Hunter et al. |
| 2003/0132913 A1 | 7/2003 | Issinski |
| 2004/0024309 A1 | 2/2004 | Ferre et al. |
| 2004/0236424 A1 | 11/2004 | Berez et al. |
| 2004/0254584 A1 | 12/2004 | Sarin et al. |
| 2006/0092022 A1 | 5/2006 | Cehelnik |
| 2006/0161871 A1 | 7/2006 | Hotelling et al. |
| 2006/0164241 A1 | 7/2006 | Makela et al. |
| 2006/0224429 A1 | 10/2006 | Mathew et al. |
| 2006/0235420 A1 | 10/2006 | Irving |
| 2006/0256090 A1 | 11/2006 | Huppi |
| 2007/0127039 A1 | 6/2007 | Njolstad |
| 2007/0175489 A1 | 8/2007 | Moctezuma et al. |
| 2008/0269599 A1 | 10/2008 | Csavoy et al. |
| 2009/0318836 A1 | 12/2009 | Stone et al. |
| 2010/0063508 A1 | 3/2010 | Borja et al. |
| 2010/0069911 A1 | 3/2010 | Borja et al. |
| 2010/0076505 A1 | 3/2010 | Borja |
| 2010/0137869 A1 | 6/2010 | Borja et al. |
| 2010/0160771 A1 | 6/2010 | Gielen et al. |
| 2010/0210939 A1 | 8/2010 | Hartmann et al. |
| 2012/0232834 A1 | 9/2012 | Roche et al. |
| 2012/0253200 A1 | 10/2012 | Stolka et al. |
| 2012/0316486 A1 | 12/2012 | Cheung et al. |

* cited by examiner

TXs 201-203
AMP 213
CONTROLLER 214
BATTERY 215
COMMUNICATIONS 216
ACCELEROMETER 217
USER INTERFACE 218
TIP SENSOR 219
BASE ATTACHMENT 205
MEMORY 208
IR TRANSMITTER 209

200

RXs 221-223
AMP 232
PROCESSOR 233
BATTERY 234
COMMUNICATIONS 235
ACCELEROMETER 236
USER INTERFACE 237
MEMORY 238
WIRELESS I/O 239
ATTACHMENT 240
PHOTO DIODE 241
LED 224

220

401 • SETUP
402 • PATIENT PREPARATION
403 • FEMUR HEAD IDENTIFACTION
404 • REGISTER FEMUR
405 • REGISTER TIBIA
406 • FEMORAL RESECTION
407 • INSTRUMENTED FEMUR CUTTING JIG
408 • TIBIAL RESECTION
409 • INSTRUMENTED TIBIAL CUTTING JIG
410 • EXTENSION GAP ASSESSMENT
411 • FEMORAL AP AND CHAMFER CUTS
412 • INSERT TRIALING (W/BALANCING)
413 • CEMENT PROSTHETIC COMPONENTS

400

600

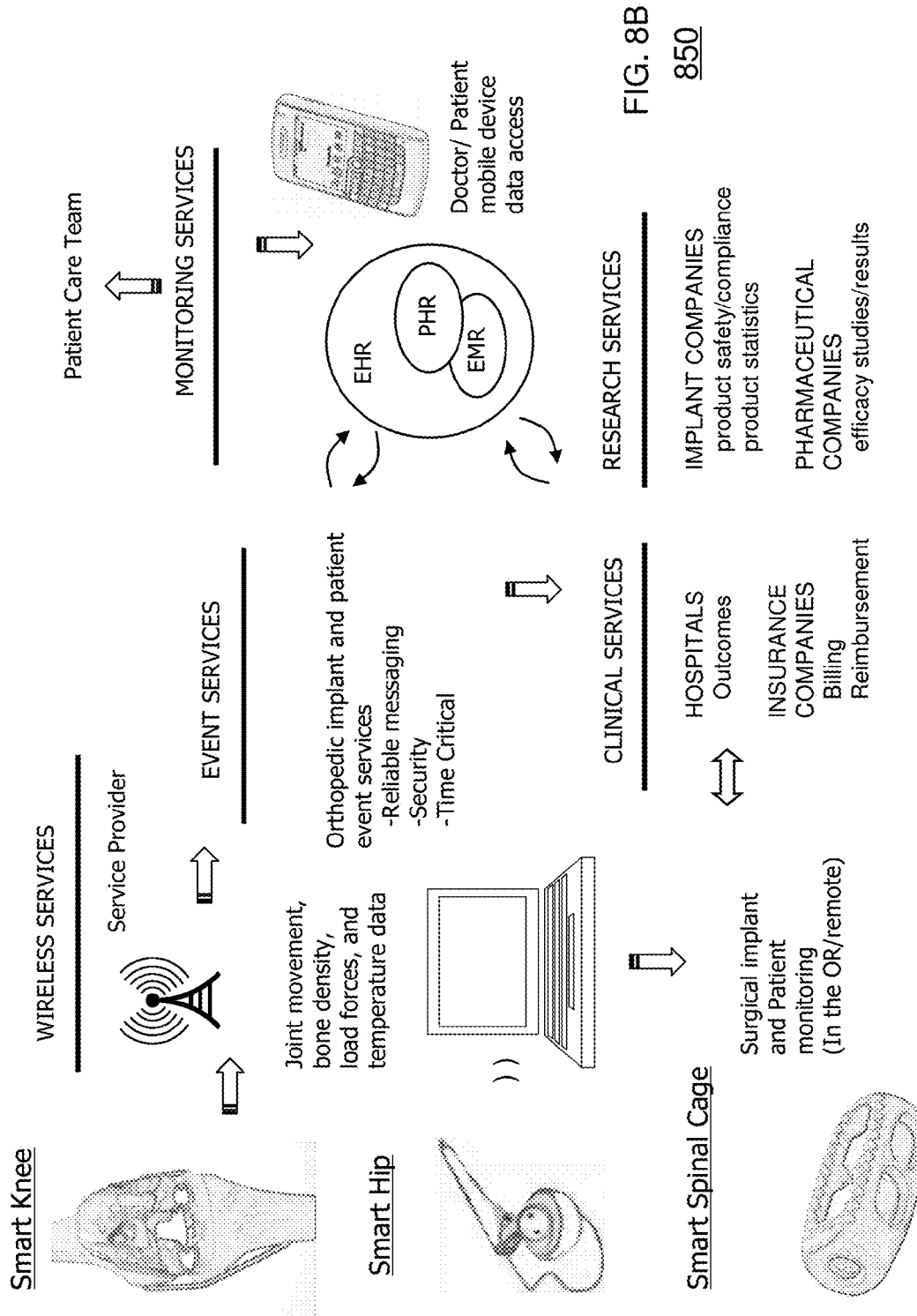

ORTHOPEDIC NAVIGATION SYSTEM WITH SENSORIZED DEVICES

CROSS-REFERENCE TO RELATED APPLICATION

This application claims the priority benefit of U.S. Provisional Patent Application No. 60/291,725 filed on Dec. 31, 2009, the entire contents of which are hereby incorporated by reference.

BACKGROUND

1. Field

The present disclosure relates generally to orthopedic medical devices, and more specifically to input pointing devices and assisted navigation surgical tools.

2. Introduction

Input pointing devices permit pointing to a point of interest. Within a navigation system its utility is a function of the sensing technology. An optical camera system generally processes captured images to determine the pointed location. An electromagnetic system generally evaluates changes in magnetic field strength. An ultrasonic sensing system evaluates received ultrasonic waveforms.

As one example, an optical navigation system can be used for a knee replacement surgery. A total knee replacement is a surgical procedure whereby the diseased knee joint is replaced with artificial material and prosthetic components. The knee is a hinge which provides motion at the point where the femur meets the tibia. During a total knee replacement, the distal end of the femur bone is removed and replaced with a femoral component. The proximal end of the tibia is also removed and replaced with a tibial component. Depending on the condition of the kneecap portion of the knee joint, a button may also be added under the kneecap surface.

During total knee replacement surgery it is imperative that the bone cuts on the femur and tibia are made to result in proper alignment. The alignment ensures proper balance and straightness of the leg. The bone cuts can be made with use of physical guides and jigs, and more recently, by way of highly accurate computer assisted systems. Commercial CAS systems are based on specific sensing principles (e.g., active or passive optical or electromagnetic) where precise intra-operative orientation is provided by high-resolution imaging techniques (e.g., computed tomography (CT), magnetic resonance imaging (MRI)). These systems generally require the placement of fiducial markers, CT or MRI imaging, data transfer to the operating room (OR), and identification and registration of the fiducials. They are also sensitive to deviations in light intensity, contrast, and reflections. When performing these preparatory and practice steps, each platform has individual needs and a number of potential deficiencies influencing the accuracy of the system.

CAS platforms generally consist of three main parts: a computer workstation, a position interface (e.g., camera system) and a passive instrument pointer. The computer workstation is the hub between the position interface and the instrument pointer. It is generally positioned away from the surgical area yet close enough to track the instrument pointer. Although it requires minimal space in the Operating Room and is sufficiently mobile it is generally a capital expense that is maintained on-site. The instruments must be sterilized with each use and the sophisticated optical components are custom made.

BRIEF DESCRIPTION OF THE DRAWINGS

FIG. 8B depicts an exemplary diagram for event services and monitoring of smart orthopedic devices in accordance with one embodiment.

DETAILED DESCRIPTION

Figure 1:
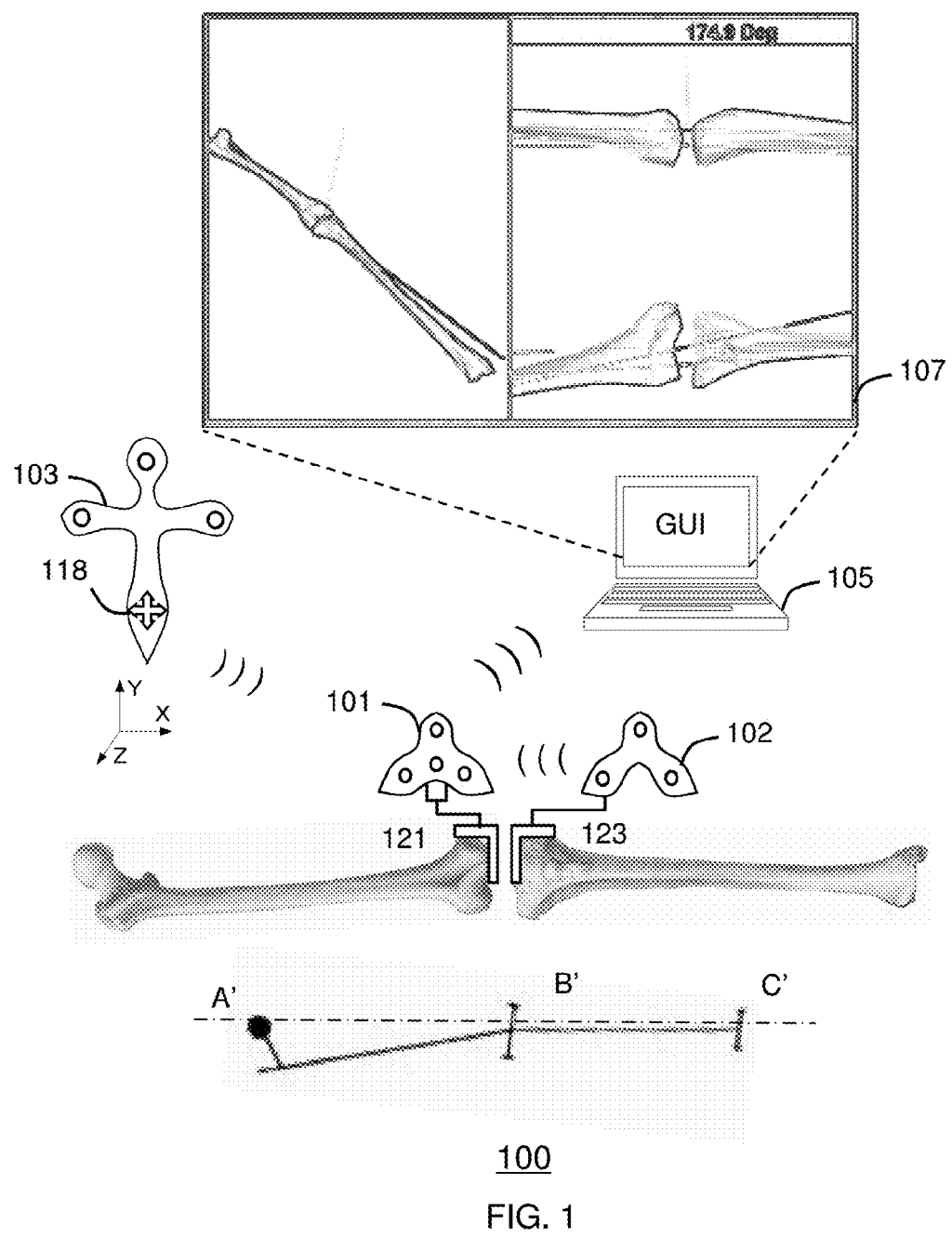
FIG. 1A depicts a navigation system and user interface in accordance with one embodiment.

While the specification concludes with claims defining the features of the invention that are regarded as novel, it is believed that the invention will be better understood from a consideration of the following description in conjunction with the drawing figures, in which like reference numerals are carried forward.

A navigation system is herein disclosed that addresses the need for low cost, portable and disposable surgical tools. The navigation system comprises compact wireless sensorized devices that communicate directly with one another; no computer workstation is required there between, which is a departure from conventional computer assisted surgery. Constructed with low-cost ultrasonic transducers and self-powered electronic components the sensorized tools provide extended surgical use and can thereafter be disposed, thereby incurring less hospital support and overhead.

In one embodiment, the sensorized tools of the navigation system comprise a receiver for placement on a first cutting jig, a mounted wand for placement on a second cutting jig, and a second wand to register points of interest on a first and second bone with respect to the cutting jigs. The receiver and wands use ultrasonic sensing to track their relative location to one another and the cutting jigs; all of which are wireless. Based on the registered points of interest, the receiver can then assess and report parameters related to the orientation of the cutting jigs for achieving cutting alignment of the first and second bone. The receiver can communicate with a display system via a wireless connection to report and visually present alignment information in real-time.

FIG. 1 depicts an exemplary embodiment of the navigation system 100 for use as an alignment tool in total knee replacement procedures. The navigation system 100 includes a receiver 101, a mounting wand 102 and a hand-held wand 103; the sensorized tools. The system can include the remote system 108 (e.g., laptop, mobile device, etc.) for presenting a graphical user interface (GUI) 107. The GUI 107 allows the user to visualize a navigated workflow with the sensorized tools and that can be customized to the orthopedic procedure. One example of providing sensory feedback in a navigated workflow with the sensorized tools is disclosed in U.S. patent application Ser. No. 12/900,878 filed Oct. 8, 2010 entitled "Navigation System and User Interface For Directing a Control Action", the entire contents of which are hereby incorporated by reference.

The receiver 101 can precisely track both wands 102-103 and report their position on the GUI 107 as part of the navigated workflow procedure. As will be discussed ahead, during the procedure, the receiver 101 is rigidly affixed to one component of a femoral cutting jig 121 for establishing cut angles on the distal femur and making corresponding femoral cuts. The mounting wand 102 can be rigidly affixed to one component of a tibial cutting jig 123 for establishing cut angles and making corresponding cuts on the proximal tibia. The wand 103 is used to register points of interest with the receiver 101. The points of interest can be on a bone or on cutting jigs 121-123 used during surgery. The navigation system 100 reports real-time alignment of the cutting jigs 121-123 and bones by way of direct communication between the wands 102-103 and the receiver 101; no computer workstation is required there between. The compact navigation system 100 assists the surgeon in establishing alignment of the cutting jigs 112 and bones and evaluating surgical process of bone alignment during and after surgery.

As one example, mechanical axis bone alignment is reported when the points of the femur head (A'), patella (B') and ankle (C') are positioned in a straight line. As will be explained ahead in more detail, the navigation system 100 intra-operatively assesses alignment of the femur and tibia bones during knee surgery by way of the rigidly attached receiver 101 and wand 102. The navigation system 100 can also transmit alignment information to wireless devices (e.g., laptop, cell phone, net book) and upload the information to a server connected to electronic medical or health care records. The system 100 assesses and reports in real-time the position of these points, or other registered points, by way of the GUI 107 on the remote system 108. It provides visual and auditory feedback related to cutting jig orientation and alignment, such as audible acknowledgements, haptic sensation (e.g., vibration, temperature), and graphical feedback (e.g., color coded line data).

Figure 2A:
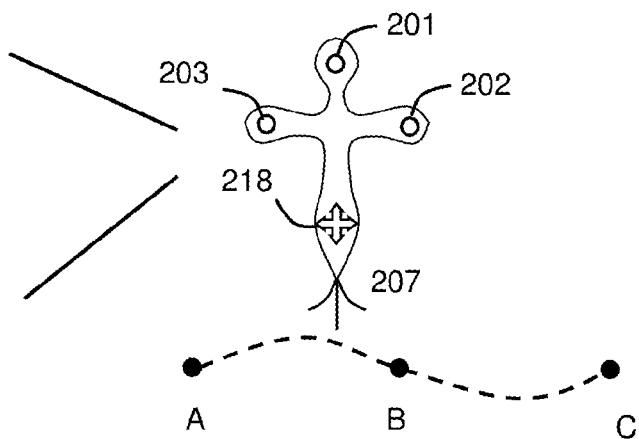
FIG. 2 depicts a receiver and wand of the navigation system in accordance with one embodiment.

FIG. 2 shows one exemplary embodiment of the wand 200 and the receiver 220, though, not all the components shown are required; fewer components can be used depending on required functionality. The receiver 220 and wand 200 and communication modes of operations there between are disclosed in U.S. patent application Ser. No. 12/900,662 entitled "Navigation Device Providing Sensory Feedback" filed Oct. 8, 2010; the entire contents of which are hereby incorporated by reference. Briefly, the current dimensions permit touchless tracking with sub millimeter spatial accuracy (<1 mm) up to approximately 2 m in distance. Either device and can be configured to support various functions (e.g, hand-held, mounted to object) and neither is limited to the dimensions described below.

The wand 200 is a hand-held device with a size dimension of approximately 10 cm in width, 2 cm depth, and an extendable length from 18 cm to 20 cm. As indicated above, the wand 200 can register points of interest (see points A, B, C), for example, along a contour of an object or surface, which can be shown in a user interface (see GUI 107 FIG. 1). As will be discussed ahead, the wand 200 and receiver 220 can communicate via ultrasonic, infrared and electromagnetic sensing to determine their relative location and orientation to one another. Other embodiments incorporating accelerometers provide further positional information.

The wand 200 includes sensors 201-203 and a wand tip 207. The sensors can be ultrasonic transducers, Micro Electro Mechanical Element (MEMS) microphones, electromagnets, optical elements (e.g., infrared, laser), metallic objects or other transducers for converting or conveying a physical movement to an electric signal such as a voltage or current. They may be active elements in that they are self powered to transmit signals, or passive elements in that they are reflective or exhibit detectable magnetic properties.

In a preferred embodiment, the wand 200 comprises three ultrasonic transmitters 201-203 for each transmitting ultrasonic signals through the air, an electronic circuit (or controller) 214 for generating driver signals to the three ultrasonic transmitters 201-203 for generating the ultrasonic signals, an user interface 218 (e.g., button) that receives user input for performing short range positional measurement and alignment determination, a communications port 216 for relaying the user input and receiving timing information to control the electronic circuit 214, and a battery 218 for powering the electronic circuit 218 and associated electronics on the wand 200. The wand 200 may contain more or less than the number of components shown; certain component functionalities may be shared as integrated devices.

Additional transmitter sensors can be included to provide an over-determined system for three-dimensional sensing. As one example, each ultrasonic transducer can perform separate transmit and receive functions. One such example of an ultrasonic sensor is disclosed in U.S. Pat. No. 7,725,288 the entire contents of which are hereby incorporated by reference. The ultrasonic sensors can transmit pulse shaped waveforms in accordance with physical characteristics of a customized transducer for constructing and shaping waveforms.

The wand tip 207 identifies points of interest on a structure, for example, an assembly, object, instrument or jig in three-dimensional space but is not limited to these. The tip does not require sensors since its spatial location in three-dimensional space is established by the three ultrasonic transmitters 201-203 arranged at the cross ends. However, a sensor element can be integrated on the tip 207 to provide ultrasound capabilities (e.g., structure boundaries, depth, etc.) or contact based sensing. In such case, the tip 207 can be touch sensitive to registers points responsive to a physical action, for example, touching the tip to an anatomical or structural location. The tip can comprise a mechanical or actuated spring assembly for such purpose. In another arrangement it includes a capacitive touch tip or electrostatic assembly for registering touch. The wand tip 207 can include interchangeable, detachable or multi-headed stylus tips for permitting the wand tip to identify anatomical features while the transmitters 201-203 remain in line-of-sight with the receiver 220 (see FIG. 1). These stylus tips may be right angled, curved, or otherwise contoured in fashion of a pick to point to difficult to touch locations. This permits the wand to be held in the hand to identify via the tip 207, points of interest such as (anatomical) features on the structure, bone or jig.

The user interface 218 can include one or more buttons to permit handheld operation and use (e.g., on/off/reset button) and illumination elements to provide visual feedback. In one arrangement, a 8-state navigation press button 209 can communicate directives to further control or complement the user interface. It can be ergonomically located on a side of the wand to permit single handed use. The wand 200 may further include a haptic module with the user interface 218. As an example, the haptic module may change (increase/decrease) vibration to signal improper or proper operation. The wand 200 includes material coverings for the transmitters 201-202 that are transparent to sound (e.g., ultrasound) and light (e.g., infrared) yet impervious to biological material such as water, blood or tissue. In one arrangement, a clear plastic membrane (or mesh) is stretched taught; it can vibrate under resonance with a transmitted frequency. The battery 218 can be charged via wireless energy charging (e.g., magnetic induction coils and super capacitors).

The wand 200 can include a base attachment mechanism 208 for coupling to a structure, object or a jig. As one example, the mechanism can be a magnetic assembly with a fixed insert (e.g., square post head) to permit temporary detachment. As another example, it can be a magnetic ball and joint socket with latched increments. As yet another example, it can be a screw post o pin to an orthopedic screw. Other embodiments may permit sliding, translation, rotation, angling and lock-in attachment and release, and coupling to standard jigs by way of existing notches, ridges or holes.

Figure 2B:
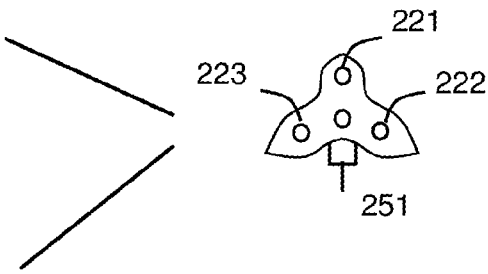

The wand 200 can further include an amplifier 213 and the accelerometer 217. The amplifier enhances the signal to noise ratio of transmitted or received signals. The accelerometer 217 identifies 3 and 6 axis tilt during motion and while stationary. The communications module 216 may include components (e.g., synchronous clocks, radio frequency 'RF' pulses, infrared 'IR' pulses, optical/acoustic pulse) for signaling to the receiver 220 (FIG. 2B). The controller 214, can include a counter, a clock, or other analog or digital logic for controlling transmit and receive synchronization and sequencing of the sensor signals, accelerometer information, and other component data or status. The battery 218 powers the respective circuit logic and components. The infrared transmitter 209 pulses an infrared timing signal that can be synchronized with the transmitting of the ultrasonic signals (to the receiver).

The controller 214 can utilize computing technologies such as a microprocessor (uP) and/or digital signal processor (DSP) with associated storage memory 108 such a Flash, ROM, RAM, SRAM, DRAM or other like technologies for controlling operations of the aforementioned components of the device. The instructions may also reside, completely or at least partially, within other memory, and/or a processor during execution thereof by another processor or computer system. An Input/Output port permits portable exchange of information or data for example by way of Universal Serial Bus (USB). The electronic circuitry of the controller can comprise one or more Application Specific Integrated Circuit (ASIC) chips or Field Programmable Gate Arrays (FPGAs), for example, specific to a core signal processing algorithm. The controller can be an embedded platform running one or more modules of an operating system (OS). In one arrangement, the storage memory may store one or more sets of instructions (e.g., software) embodying any one or more of the methodologies or functions described herein.

The receiver 220 comprises a processor 233 for generating timing information, registering a pointing location of the wand 200 responsive to the user input, and determining short range positional measurement and alignment from three or more pointing locations of the wand 200 with respect to the receiver 220. The receiver has size dimensions of approximately 2 cm width, 2 cm depth, and a length of 10 cm to 20 cm. It includes a communications interface 238 for transmitting the timing information to the wand 200 that in response transmits the first, second and third ultrasonic signals. The ultrasonic signals can be pulse shaped signals generated from a combination of amplitude modulation, frequency modulation, and phase modulation. Three microphones 221-223 each receive the first, second and third pulse shaped signals transmitted through the air. The receiver 220 shape can be configured from lineal as shown, or in more compact arrangements, such as a triangle shape. One example of a device for three-dimensional sensing is disclosed in U.S. patent application Ser. No. 11/683,410 entitled "Method and Device for Three-Dimensional Sensing" filed Mar. 7, 2007 the entire contents of which are hereby incorporated by reference.

The memory 238 stores the ultrasonics signals and can produce a history of ultrasonic signals or processed signals. It can also store wand tip positions, for example, responsive to a user pressing the button to register a location. The wireless communication interface (Input/Output) 239 wirelessly conveys the positional information and the short range alignment of the three or more pointing locations to a remote system. The remote system can be a computer, laptop or mobile device that displays the positional information and alignment information in real-time as described ahead. The battery powers the processor 233 and associated electronics on the receiver 220. The receiver 200 may contain more or less than the number of components shown; certain component functionalities may be shared or therein integrated.

Additional ultrasonic sensors can be included to provide an over-determined system for three-dimensional sensing. The ultrasonic sensors can be MEMS microphones, receivers, ultrasonic transmitters or combination thereof. As one example, each ultrasonic transducer can perform separate transmit and receive functions. One such example of an ultrasonic sensor is disclosed in U.S. Pat. No. 7,414,705 the entire contents of which are hereby incorporated by reference. The receiver 220 can also include an attachment mechanism 240 for coupling to bone or a jig by way of the pin 281. As one example, the mechanism 240 can be a magnetic assembly with a fixed insert (e.g., square post head) to permit temporary detachment. As another example, it can be a magnetic ball and joint socket with latched increments.

The receiver 220 can further include an amplifier 232, the communications module 238, an accelerometer, and processor 233. The processor 233 can host software program modules such as a pulse shaper, a phase detector, a signal compressor, and other digital signal processor code utilities and packages. The amplifier 232 enhances the signal to noise of transmitted or received signals. The processor 233 can include a controller, counter, a clock, and other analog or digital logic for controlling transmit and receive synchronization and sequencing of the sensor signals, accelerometer information, and other component data or status. The accelerometer 236 identifies axial tilt (e.g., 3/6 axis) during motion and while stationary. The battery 234 powers the respective circuit logic and components. The receiver includes a photo diode 241 for detecting the infrared signal and establishing a transmit time of the ultrasonic signals to permit wireless infrared communication with the wand.

The communications module 238 can include components (e.g., synchronous clocks, radio frequency 'RF' pulses, infrared 'IR' pulses, optical/acoustic pulse) for local signaling (to wand 102). It can also include network and data components (e.g., Bluetooth, ZigBee, Wi-Fi, GPSK, FSK, USB, RS232, IR, etc.) for wireless communications with a remote device (e.g., laptop, computer, etc.). Although external communication via the network and data components is herein contemplate, it should be noted that the receiver 220 can include a user interface 237 to permit standalone operation. As one example, it can include 3 LED lights 224 to show three or more wand tip pointing location alignment status. The user interface 237 may also include a touch screen or other interface display with its own GUI for reporting positional information and alignment.

The processor 233 can utilize computing technologies such as a microprocessor (uP) and/or digital signal processor (DSP) with associated storage memory 108 such a Flash, ROM, RAM, SRAM, DRAM or other like technologies for controlling operations of the aforementioned components of the terminal device. The instructions may also reside, completely or at least partially, within other memory, and/or a processor during execution thereof by another processor or computer system. An Input/Output port permits portable exchange of information or data for example by way of Universal Serial Bus (USB). The electronic circuitry of the controller can comprise one or more Application Specific Integrated Circuit (ASIC) chips or Field Programmable Gate Arrays (FPGAs), for example, specific to a core signal processing algorithm or control logic. The processor can be an embedded platform running one or more modules of an operating system (OS). In one arrangement, the storage memory 238 may store one or more sets of instructions (e.g., software) embodying any one or more of the methodologies or functions described herein.

In a first arrangement, the receiver 220 is wired via a tethered electrical connection (e.g., wire) to the wand 200. That is, the communications port of the wand 200 is physically wired to the communications interface of the receiver 220 for receiving timing information. The timing information from the receiver 220 tells the wand 200 when to transmit and includes optional parameters that can be applied to pulse shaping. The processor on the receiver 220 employs this timing information to establish Time of Flight measurements in the case of ultrasonic signaling with respect to a reference time base.

In a second arrangement, the receiver 220 is communicatively coupled to the wand 200 via a wireless signaling connection. A signaling protocol is disclosed in U.S. patent application Ser. No. 12/900,662 entitled "Navigation Device Providing Sensory Feedback" filed Oct. 8, 2010; the entire contents of which are hereby incorporated by reference. An infrared transmitter 209 on the wand 200 transmits an infrared timing signal with each transmitted pulse shaped signal. It pulses an infrared timing signal that is synchronized with the transmitting of the ultrasonic signals to the receiver. The receiver 302 can include a photo diode 241 for determining when the infrared timing signal is received. In this case the communications port of the wand 200 is wirelessly coupled to the communications interface of the receiver 220 by way of the infrared transmitter and the photo diode for relaying the timing information to within microsecond accuracy (~1 mm resolution). The processor on the receiver 220 employs this infrared timing information to establish the first, second and third Time of Flight measurements with respect to a reference transmit time.

Figures 3, 4:
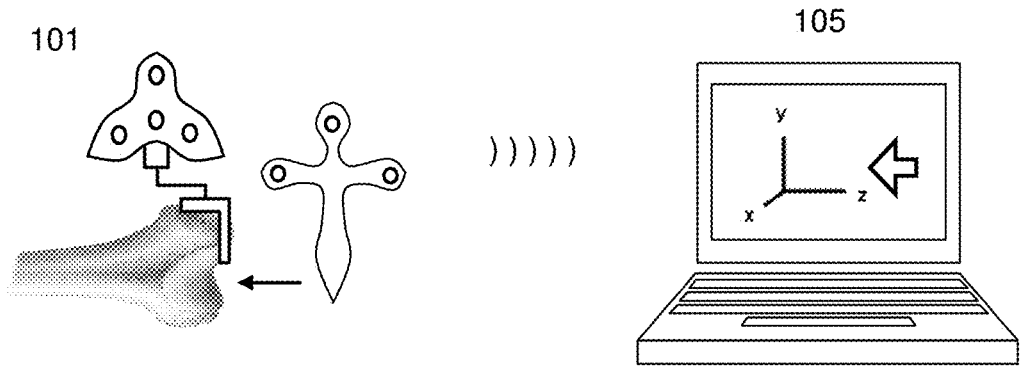
FIG. 3 depicts an illustration for registering points of interest in accordance with one embodiment.
FIG. 4 depicts an outline of a surgical workflow procedure in accordance with one embodiment.
Figure 5A:
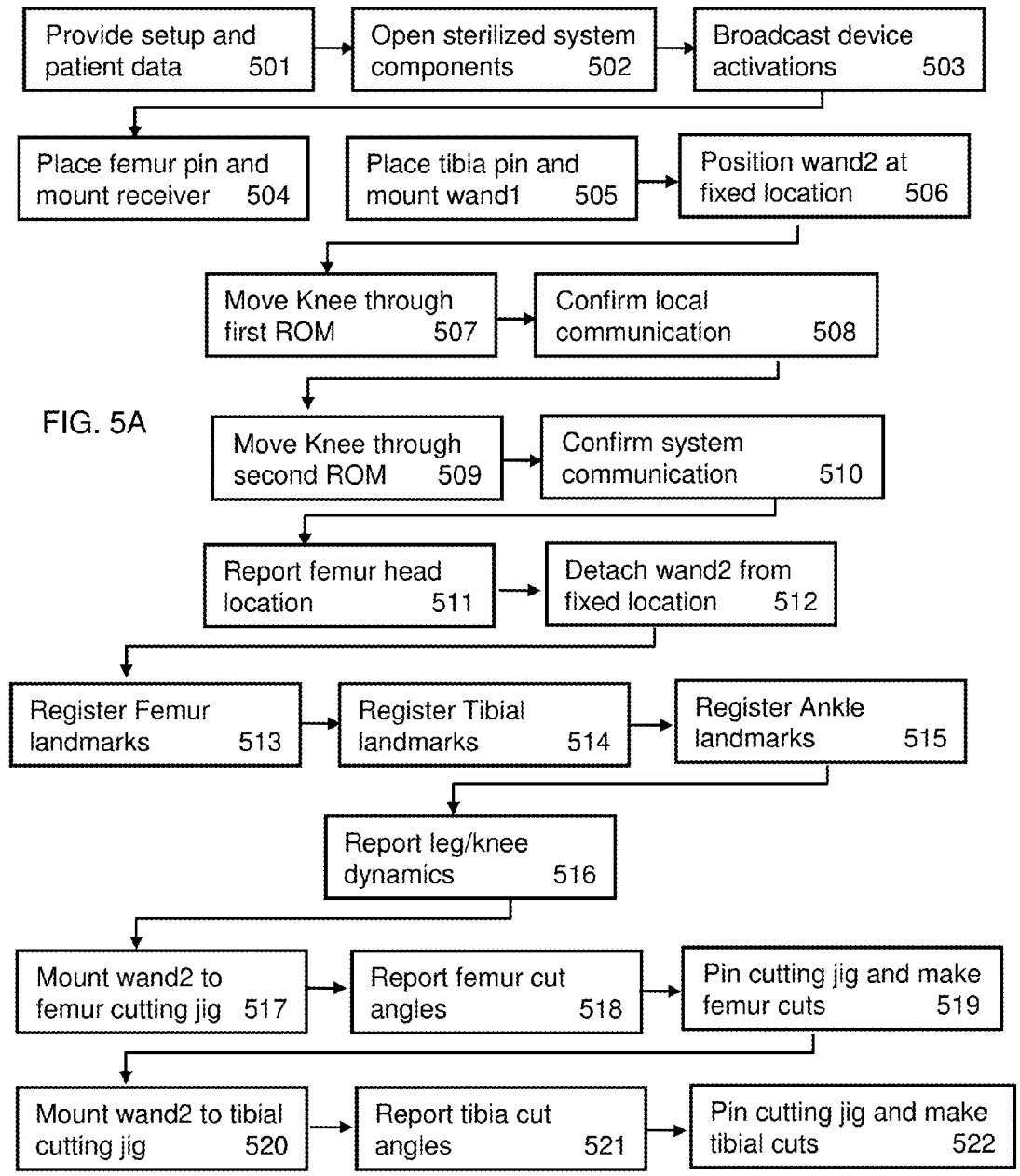
FIG. 5A depicts a first set of method steps directed to the surgical workflow procedure in accordance with one embodiment.
Figure 5B:
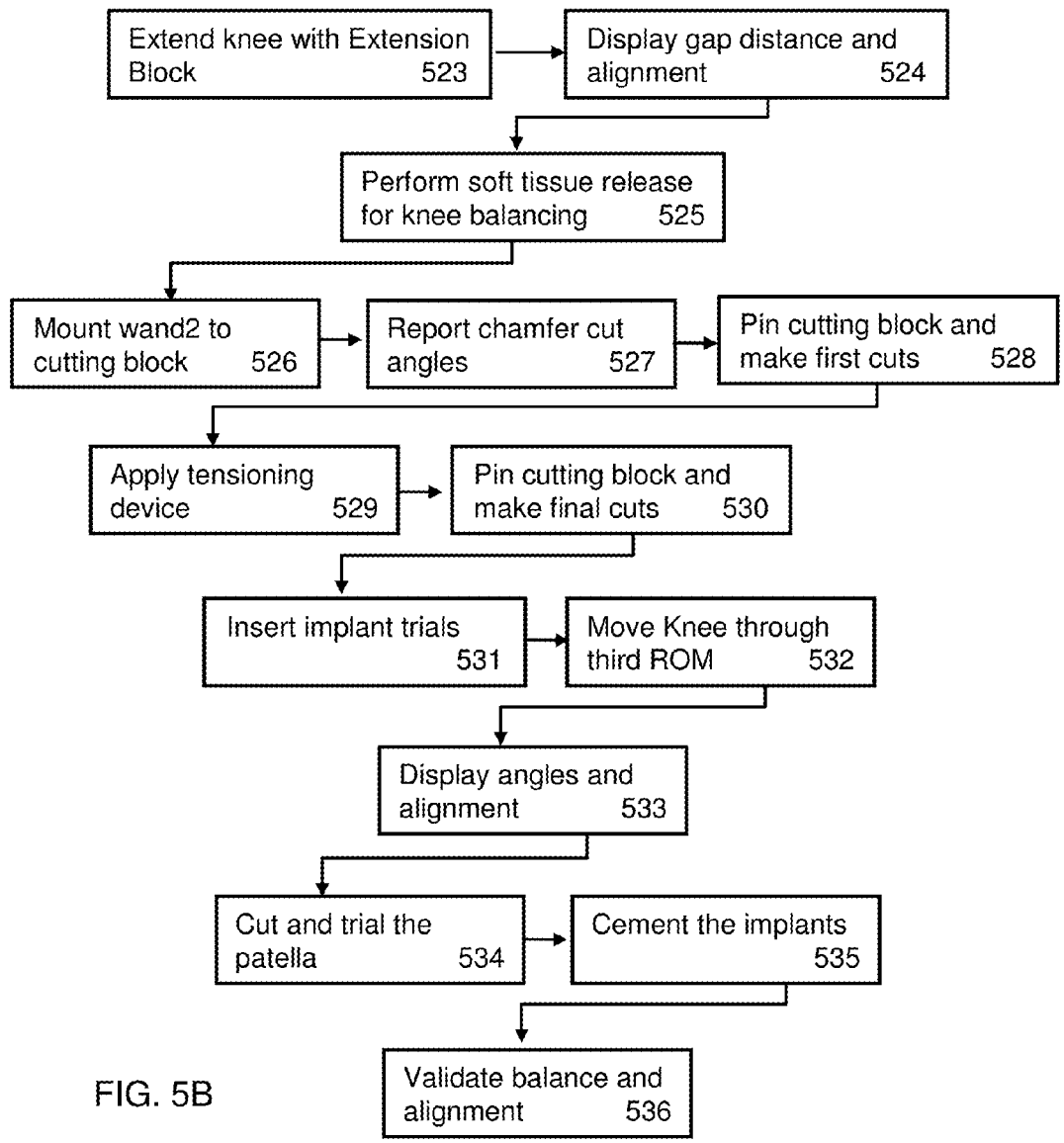
FIG. 5B depicts a second set of method steps directed to the surgical workflow procedure in accordance with one embodiment.

FIG. 3 depicts an exemplary illustration using the wand 103 to register anatomical features on the bone. During registration, one of the wand tips 207 (see FIG. 2) is touched to the distal bone center, to register that location with the receiver 101. The remote system 108 visually shows the movement of the wand 103 in 3D with respect to the receiver 101 and the registered points. The wand 103 and the receiver 101 can communicate via a local communications protocol (e.g. optical/ultrasonic pulsing) apart from the network communication (e.g., Bluetooth, Wi-Fi) between the receiver 101 and the remote system 108. In a master-slave configuration, the wand 103 serves as the slave to inform the receiver 101 of the points of interest, and the receiver 101 serves as the master for communication of the alignment information to the remote system 108.

FIG. 4 depicts a high-level exemplary workflow 400 for a sensory assisted surgical procedure according to one embodiment. Briefly, the workflow 400 is directed to a total knee replacement surgery. During the workflow, the surgeon desires to obtain a neutral mechanical axis. This is defined as a straight line extending from the patients femoral head, through the center of the knee to the center of the ankle (see line ABC, FIG. 1). The proper knee joint alignment is critical for a patient's knee function and performance.

The navigation system 100 assists the surgeon in making navigated knee replacements an easy and successful procedure. It visually guides the surgeon towards proper alignment and making bone cuts to achieve a neutral mechanical axis. The workflow 400 can be practiced with more or less than the number of steps shown and is not limited to the order shown. The workflow 400 can also be modified to include additional steps such as performing a combined balance and alignment evaluation during insert trialing as will be discussed ahead. Completion of the workflow steps during surgical operation may be on the order of 8-7 minutes. Briefly, low-level method steps 401-409 of the workflow are described ahead in FIG. 8A. Low-level method steps 410-413 of the workflow are described ahead in FIG. 8B.

The high-level work flow 400 comprises:
401 Setup
402 Patient preparation
403 Femur head identification
404 Register femur
408 Register tibia
406 Femoral resection
407 Instrumented femoral cutting jig
408 Tibial resection
409 Instrumented tibial cutting jig
410 Extension gap assessment
411 Femoral AP and chamfer cuts
412 Insert trialing
413 Cement prosthetic components FIG. 8 depicts the low-level portion of the workflow steps 401-409 of workflow 400 of FIG. 4. At step 801, setup information and patient data is provided to a first GUI page for commencing the workflow 400. It can be input to the remote system 108 which in the present embodiment hosts the GUI 107. The GUI 107 hosts the customized workflow 400 for the total knee replacement procedure. An example of a navigated workflow is disclosed in U.S. patent application Ser. No. 12/900,878, the entire contents of which are hereby incorporated by reference. The patients name and surgery information can be entered into the GUI 107. It also documents a time in and time out to confirm the patient with the procedure.

At step 802 the sterilized components (sensorized tools) of the navigation system 100 are opened, activated and calibrated. This includes: receiver 101, mounted wand 102 and hand-held wand 103 (hereinafter system components). The calibration is a short procedure where the system components are validated for user requirement accuracy. At step 803 the system components broadcast their activation. The GUI 107 indicates (e.g., visual, auditory, and/or haptic) that the system components are on and operational according to specification.

After the patient is prepped for surgery the GUI 107 transitions to a femur registration page with information to provide visual guidance. The knee is opened with a longitudinal incision to expose the knee joint. Retractors are applied to protect soft tissue. At step 804 a Femur Pin 281 is placed in the distal femur. The receiver 101 is mounted to the femur pin 281 (in or out of incision). As an example of affixing, a screw post can include a detachable magnetic assembly to temporarily couple the receiver 101 to the bone. Other affixing means are herein contemplated. The receiver board is angled medially the receiver 101 to allow line-of-sight to the mounted wand 102.

The GUI transitions to a tibia registration page. At step 808 a tibial pin (like pin 281) is pinned in the proximal tibia or midway on the tibia. The mounted wand 102 is mounted to the tibial pin to be line-of-sight with the receiver 101. Similar mounting mechanisms can be included to ensure a rigid attachment of the mounted wand 102 to tibial pin.

At step 806 the other hand-held Wand 103 (hereinafter Wand) is temporarily mounted to a stationary (overhead) stand and angled towards the receiver 101 (See FIG. 1). Wand 103 serves as a reference location for the receiver 101 when the receiver 101 is moving, as will be seen ahead. The Wand 103 can be placed within close proximity of the receiver 101, for example, within 2 meters, and out of the way of the mechanics of the procedure.

In the next step 807, the tibia is moved through a first range of motion (ROM1) from extension (straight leg) to flexion (knee bent ~90 degrees) to ensure the receiver 101 and mounted wand 102 remain sufficiently in line-of-sight; approximately –60 to 60 degrees face-to-face incident angles. The GUI 107 confirms local line of sight between the receiver 101 and mounted wand 102 at step 808. The GUI can provide sensory feedback to visually indicate line-of-site conditions, for example, turning red or green accordingly.

Next, the GUI 107 transitions to a femoral Identification (ID) page. It instructs the surgeon to place the hip in flexion and apply gentle femoral rotation. This motion is applied at step 809 to allow the receiver 101 to identify the femoral head (e.g., hip joint). One example of determining the femur head center is disclosed in U.S. patent application Ser. No. 12/900,955 filed Oct. 8, 2010 entitled "Orthopedic Method and System for Mapping an Anatomical Pivot Point, the entire contents of which are included by reference in entirety. Another is based on pivot point determination in U.S. Pat. No. 7,788,607, the entire contents of which are hereby incorporated by reference. The GUI 107 visually confirms this second range of motion (ROM) at step 810, for example, by indicating a green status for line-of-sight. Line of sight is approximately ±60 degrees conical for certain user requirement precision, but can approach up to +90 degrees otherwise. It indicates a red status when the ROM is outside the line-of-sight. At step 811 GUI 107 informs the surgeon when the femoral head is registered and located within accuracy—it shows data collection, timestamp, and check points. The femur head establishes a first point for mechanical axis alignment (see FIG. 1, point A of line ABC).

Once the GUI 107 confirms femur head identification, the wand 103 is removed from the stationary (overhead) stand at step 812. It is thereafter used to register the anatomical landmarks during the workflow procedure. At step 813, the GUI instructs the surgeon to register distal femoral center with Wand tip 207. The GUI also indicate if the Wand 103 falls out of the line-of-sight and/or requires surgeon to re-register landmarks. The following points are registered:
  Lowest points on distal femoral condyles (medial and lateral)
  Epicondyles
  Anterior cortex of distal femur
  Posterior femoral condyles (PFC) (medial and lateral).

At step 814, the GUI instructs the surgeon to use the wand 103 to register the following tibial landmarks:
  Center of tibia (base of ACL)
  Deepest points on proximal medial and lateral tibial plateau At step 818, the GUI instructs the surgeon to use the wand 103 to register the following ankle landmarks:
  Medial malleolus
  Lateral malleolus During the registration above, the GUI visually shows the registered points on the display in 3D, but is not limited to only the registration of these points. It also displays the desired mechanical axis of the leg for the leg in extension case (see FIG. 1, line ABC).

Figure 6A:
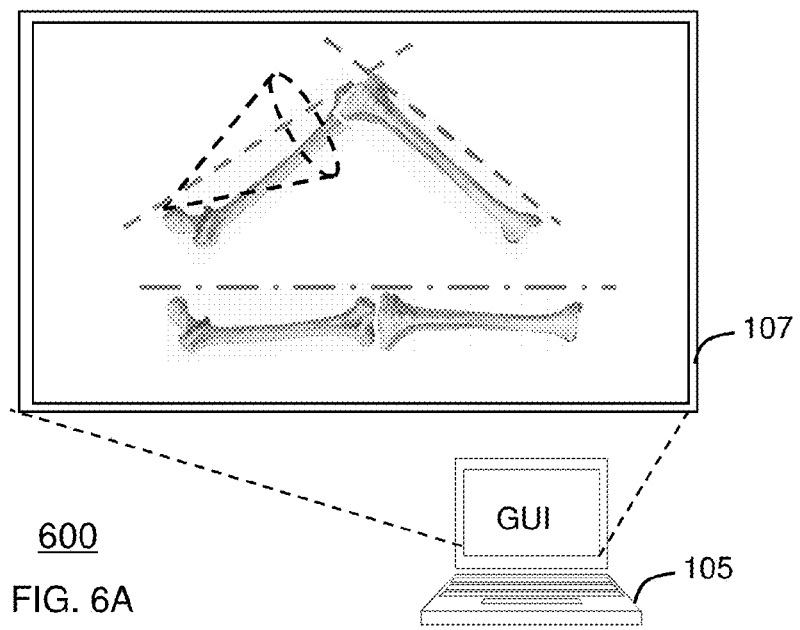
FIG. 6A illustrates a GUI providing visual feedback of the surgical workflow procedure in accordance with one embodiment.

At step 816, dynamic knee data and leg information is captured related to the patient's current leg alignment and knee flexion. This information is recorded and reported. The knee flexion is specified by an angle indicating the amount of hyperextension through full bending of the knee (flexion). This angle can be between –10 to +120 degrees depending on the patient's condition. The GUI 107 instructs the surgeon to place the knee in extension and hold the leg steady to register the extension angle and mechanical axis. The knee is them moved through a full ROM1 while the receiver 101 collects flexion data through minimum to maximum range. The GUI 107 tracks and reports the femur and tibia during ROM1 as shown in FIG. 6A.

Figure 6B:
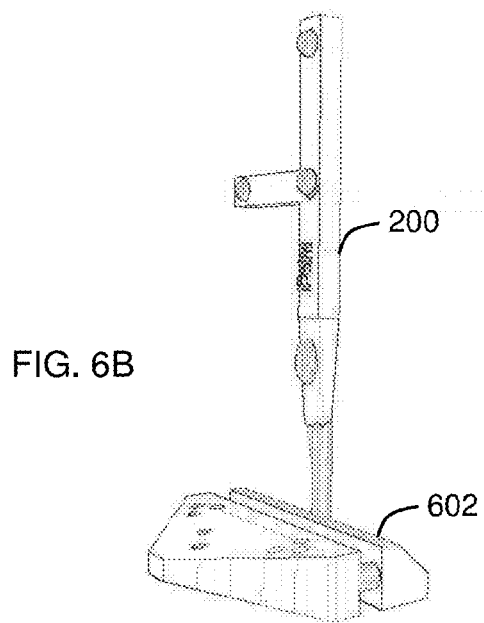
FIG. 6B illustrates an instrumented cutting jig for use in the surgical workflow procedure in accordance with one embodiment.

Next, the GUI 107 transitions to a femoral resection and instrumented cutting jig page. The knee is placed in flexion. During this step, the tibial wand 102 may be temporarily removed from the tibial pin if it is in the way, but remounted in a later step ahead. At step 817, the wand 103 is then mounted to the femoral cutting jig (see FIG. 1, 121). FIG. 6B shows one example of a wand coupled to a cutting jig component 602 although other embodiments are herein contemplated. In the current example, the component 602 can be coupled to cutting jig 121 of FIG. 1. This permits the receiver 101 to track translation and orientation of the cutting jig component 602 for establishing femoral cutting angles as shown in step 818 to make femoral cuts. During navigation of the cutting jig 602, the GUI displays the following:
  Distal femur and registered femoral features
  Tracking of the Femoral Cutting Jig
  Cutting planes with depth of cut to each registered distal condyles.
  Flexion/extension angle of cutting plane relative to femoral mechanical axis, and
  Varus-valgus angle of cutting plane relative to femoral mechanical axis.

At step 819, the Femoral Cutting Jig 121 is positioned and navigated in view of the GUI and pinned securely to the distal femur for the desired cutting plane. The distal end of the femur is then cut. The Femoral Cutting Jig 121 is then unpinned and placed bottom flat surface on the cut distal femoral surface to verify cut accuracy; that is, it is laid against the cut. The GUI 107 report distal femoral cut accuracy based on the positioning of the wand 102 mounted (sensorized) cutting jig 121.

The GUI then transitions to the tibial resection and instrumented cutting jig page. The wand 102 is then removed from the femoral cutting jig 121 and attached to the tibial cutting jig 123 at step 820. During this time, the other mounted wand 103 may be remounted to the tibial pin 281 if it was previously removed. This permits the receiver 101 to track translation and orientation of the cutting jig 123 for establishing tibial cutting angles as shown in step 821 to make tibial cuts. The GUI displays the following:

Tibia and registered tibial features
    Tibial Cutting Jig on the Display
    Cutting plane with depth of cut to lowest points on medial and lateral tibial plateau.
    Varus-valgus angle of cutting plane relative to Tibial mechanical axis, and
    anterior/posterior slope relative to the tibial mechanical axis.

At step 822, the Tibial Cutting Jig 123 is positioned and navigated in view of the GUI and pinned securely to the tibia for the desired cutting plane. The proximal end of the tibia is then cut. Bony or meniscal remnants are removed from the cut area. The Tibial Cutting Jig 123 is then unpinned and placed bottom flat surface on the cut proximal tibial surface to verify cut accuracy; it is laid against the cut. The GUI 107 report proximal tibial cut accuracy based on the positioning of the wand 102 mounted (sensorized) cutting jig 123.

Figure 8A:
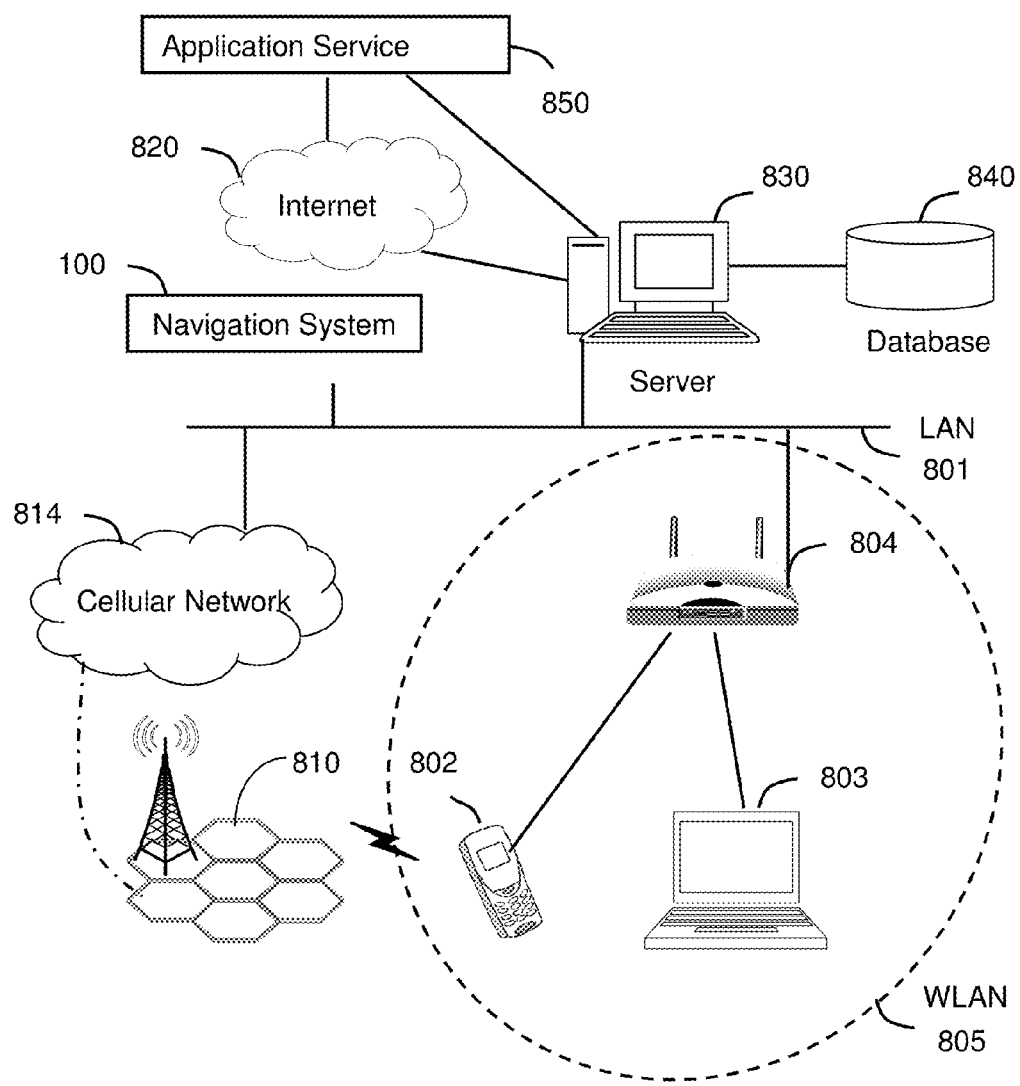
FIG. 8A depicts an exemplary communication system deploying the navigation system in accordance with one embodiment.

FIG. 8B depicts the low-level portion of the workflow steps 410-413 of workflow 400 of FIG. 4 and continues from FIG. 8A above. At shown in step 823, upon completion of the tibial cut, the knee is extended with an extension block to assess extension gap and confirm gap resection. The extension gap is a volumetric void between the distal femur end and the proximal tibia end; a portion of the void was created due to the cutting of the femur bone end and the tibial bone end which had partially occupied that region prior to cutting.

The GUI 107 at step 824 displays the measured gap distances and varus/valgus alignment. These measurements can be verified by the navigation system 100 in addition to the extension block. The gap distance is a function of knee flexion and indicates the flexibility and strength of the medial and lateral knee tendons. The gap distance in extension (leg straight) can differ from the gap distance in flexion (leg bent) by a few millimeters. It also provides an indication of a permitted level of soft tissue release for achieving proper balance and alignment which is performed in step 828. The gap distance is also assessed in order to determine appropriate chamfer cutting angles on the distal femur and proximal tibia and trial insert sizes.

The GUI 107 then transitions to a femoral Anterior-Posterior (AP) and chamfer cuts page. The knee is placed in flexion. At step 826, the wand 103 is mounted to a 4in1 cutting block; a sophisticated jig that provides four different cutting angles in one block. The AP position and rotary position of the 4in1 cutting block is then defined in view of the GUI 107. The GUI shows the location and orientation of the (sensorized) 4in1 block relative to the cutting planes and registered anatomical features. At step 827, the 4in1 block is positioned and navigated in view of the GUI 107 and pinned securely for the desired cutting plane. The AP cut is made and thereafter the chamfer cuts are made on the distal femur end as shown in step 828. Upon making the first series of cuts, a tensioning device is then applied off the tibia at step 829 to distract the knee joint to cause the ligaments to rotate the femur until it is parallel to the cut tibial plateau (Ligament Tensioning technique). The 4in1 block is then positioned and navigated in view of the GUI 107 with the incorporated AP positioning. The 4in1 block is pinned securely for the desired cutting plane and the final AP and chamfer cuts are made at step 830.

Figure 6C:
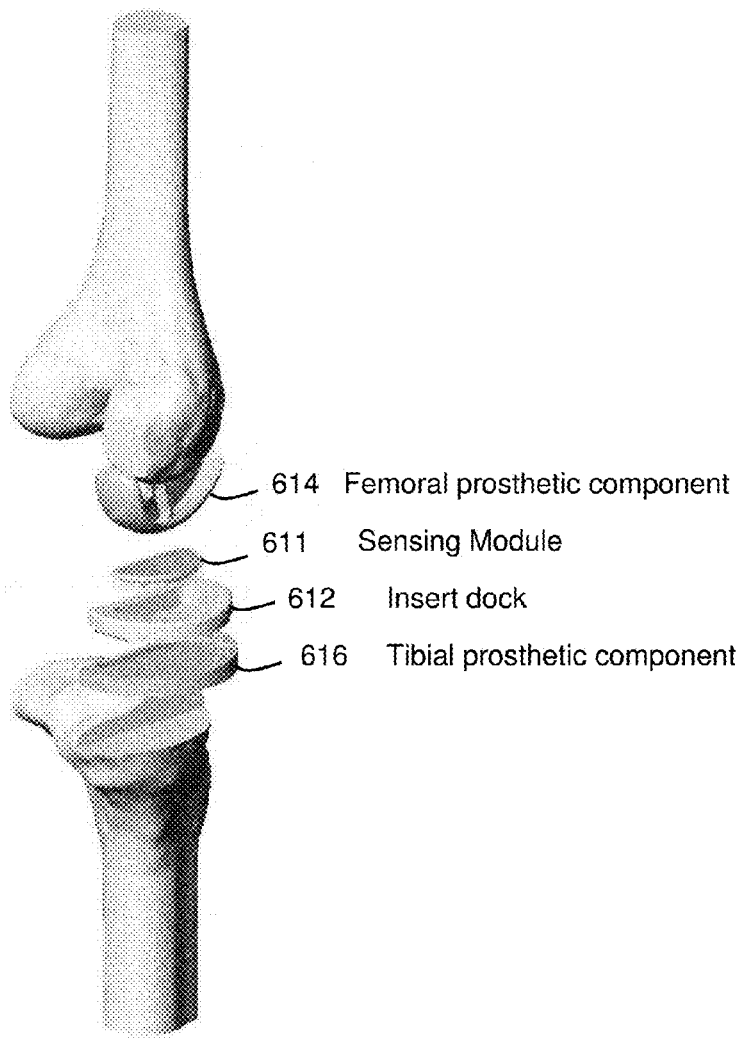
FIG. 6C depicts an exemplary illustration of a sensing module used with the navigation system in accordance with one embodiment.

The GUI 107 then transitions to an insert trialing page which guides the surgeon through selecting trial inserts. At step 831, the femoral and tibial implant trials with tibial insert trial are inserted. During this procedure, a load sensing insert device can also be embedded within the tibial trial insert to assess balance. FIG. 6C illustrates an exemplary relationship among such components of a prosthetic knee implant: the sensing module 611, the femoral prosthetic component 614, tibial prosthetic (tray or plate) component 616, and the tibial insert dock 612. The Load Sensing Insert Device 611 provides a concave surface against which the outer condylar articulating surface of the femoral prosthetic component 614 rides relative to the tibia prosthetic component 616. Examples of a load sensing insert sensing module are described in ORTHO-01US, U.S. patent application Ser. No. 12/825,638 entitled "SYSTEM AND METHOD FOR ORTHOPEDIC LOAD SENSING INSERT DEVICE", ORTHO-07US, U.S. patent application Ser. No. 12/825,724 entitled "WIRELESS SENSING MODULE FOR SENSING A PARAMETER OF THE MUSCULAR-SKELETAL SYSTEM", ORTHO-10US, U.S. patent application Ser. No. 12/825,770 entitled "INTEGRATED SENSOR FOR MEDICAL APPLICATIONS", ORTHO-27US, U.S. patent application Ser. No. 12/826,329 entitled "SENSING MODULE FOR ORTHOPEDIC LOAD SENSING INSERT DEVICE" all filed Jun. 29, 2010; the entire contents of each which are hereby incorporated by reference herein. In such a configuration, the navigation system 100 reports combined balance and alignment information by way of the GUI 107.

At step 832, the knee is removed through a third range of motion (ROM3) to assess implant stability, slipping and proper fit. During the ROM3, the GUI 107 displays the knee with extension angle and mechanical axis as shown in step 833. It also displays combined balance and alignment information when the sensing insert device 800 above (see FIG. 8) is included therein. The GUI 107 reports knee flexion, balance and alignment while the knee is moved through maximal flexion through extension to hyperextension as permitted. During ROM3, the knee may be subluxed posteriorly in flexion in view of the GUI 107 to define any posterior instability. At step 834, the patella is cut and trialed. The femur bone and tibia are then prepped for implant and cemented in at step 838 and the final poly is inserted. The knee is moved through a final Range of Motion in view of the GUI displaying the extension angle and mechanical axis to validate balance and alignment as shown in step 836.

Figure 7:
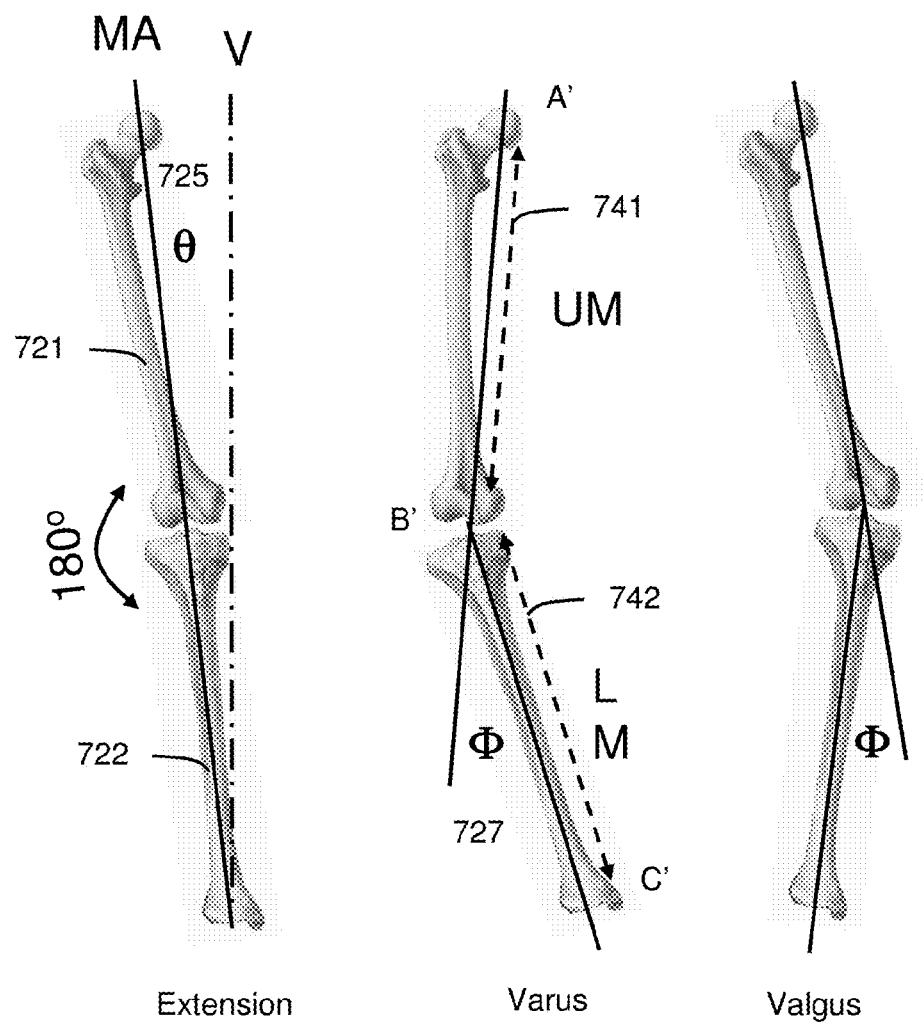
FIG. 7 depicts an illustration of anatomical deviations with respect to mechanical axis alignment.

FIG. 7 shows alignment along a mechanical axis of a leg for normal and abnormal conditions. In extension, the femur 721 and tibia 722 of the leg are aligned along the mechanical axis (MA). The MA is approximately θ~=6 degrees 728 from the vertical (V) at the ankle; and approximately 18-18 degrees from the vertical (V) at the knee (Q-angle) for a straight leg in standing position. As illustrated in the center subplot, a varus deformity is an outward angulation of the distal segment of a bone or joint with an alignment angle (or error) described by −Φ 727. As illustrated in the right subplot a valgus deformity is a term for the inward angulation of the distal segment of a bone or joint with an alignment angle (or error) described by +Φ 727. The system 100 reports the alignment angle Φ 727 between the first line 741 and the second line 742 as part of the positional location (information). The first line 741 is defined by the first point A' (registered at a first time) and a second point B' (registered at a second time). The second line 742 is defined by the pointing location of the Wand 200 at the second point B' and a third point C' at a third time. The system 100 can include multiple points for determining alignment and is not limited to a 3-point profile.

As previously indicated the receiver 200 itself can display alignment information or report the information to remote system to provide visualization. As one example, the LED lights 224 on the Receiver 302 illuminate in accordance with a detected alignment. A single multi-color LED will turn green for perfect alignment (0°), turn yellow if less than 2°, and turn red if alignment is off by 3° or more. With single color LEDS, a varus condition will illuminate the corresponding medial (inside) LED, a valgus condition will illuminate the corresponding lateral (outside) LED, and an alignment less than 1° will show all LEDS green. Other illumination patterns are herein contemplated and are not limited to those described. Similarly, the GUI 307 can report alignment information via text representation of the alignment error or by color coding displayed line segments.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

For example, referring to FIG. 8, a communication network 800 for alignment detection and reporting is shown. Briefly, the communication network 800 broadens the data connectivity of the navigation system 100 shown in FIG. 1 to other devices or services. For instance, the alignment detection and reporting aspects of the navigation system 100 can be communicatively coupled to the communications network 800 and any other associated systems or services.

As one example, the navigation system 100 can share its parameters of interest (e.g., angles, alignment, displacement, movement, orientation, rotation, and acceleration) with remote services or providers, for instance, to analyze or report on surgical status or outcome. This data can be shared for example with a service provider to monitor progress or with plan administrators for surgical monitoring purposes or efficacy studies. The communication network 800 can further be tied to an Electronic Medical Records (EMR) system to implement health information technology practices. In other embodiments, the communication network 800 can be communicatively coupled to HIS Hospital Information System, HIT Hospital Information Technology and HIM Hospital Information Management, EHR Electronic Health Record, CPOE Computerized Physician Order Entry, and CDSS Computerized Decision Support Systems. This provides the ability of different information technology systems and software applications to communicate, to exchange data accurately, effectively, and consistently, and to use the exchanged data.

The communications network 800 can provide wired or wireless connectivity over a Local Area Network (LAN) 801, a Wireless Local Area Network (WLAN) 808, a Cellular Network 814, and/or other radio frequency (RF) system (see FIG. 4). The LAN 801 and WLAN 808 can be communicatively coupled to the Internet 820, for example, through a central office. The central office can house common network switching equipment for distributing telecommunication services. Telecommunication services can include traditional POTS (Plain Old Telephone Service) and broadband services such as cable, HDTV, DSL, VoIP (Voice over Internet Protocol), IPTV (Internet Protocol Television), Internet services, and so on.

The communication network 800 can utilize common computing and communications technologies to support circuit-switched and/or packet-switched communications. Each of the standards for Internet 820 and other packet switched network transmission (e.g., TCP/IP, UDP/IP, HTML, HTTP, RTP, MMS, SMS) represent examples of the state of the art. Such standards are periodically superseded by faster or more efficient equivalents having essentially the same functions. Accordingly, replacement standards and protocols having the same functions are considered equivalent.

The cellular network 814 can support voice and data services over a number of access technologies such as GSM-CPRS, EDGE, CDMA, UMTS, WiMAX, 2G, 3G, 4G, WAP, software defined radio (SDR), and other known technologies. The cellular network 814 can be coupled to base receiver 810 under a frequency-reuse plan for communicating with mobile devices 802.

The base receiver 810, in turn, can connect the mobile device 802 to the Internet 820 over a packet switched link. The internet 820 can support application services and service layers for distributing data from the load sensing system 100 to the mobile device 802. The mobile device 802 can also connect to other communication devices through the Internet 820 using a wireless communication channel.

The mobile device 802 can also connect to the Internet 820 over the WLAN 808. Wireless Local Access Networks (WLANs) provide wireless access within a local geographical area. WLANs are typically composed of a cluster of Access Points (APs) 804 also known as base stations. The navigation system 100 can communicate with other WLAN stations such as laptop 803 within the base station area. In typical WLAN implementations, the physical layer uses a variety of technologies such as 802.11b or 802.11g WLAN technologies. The physical layer may use infrared, frequency hopping spread spectrum in the 2.4 GHz Band, direct sequence spread spectrum in the 2.4 GHz Band, or other access technologies, for example, in the 8.8 GHz ISM band or higher ISM bands (e.g., 24 GHz, etc).

By way of the communication network 800, the navigation system 100 can establish connections with a remote server 830 on the network and with other mobile devices for exchanging data. The remote server 830 can have access to a database 840 that is stored locally or remotely and which can contain application specific data. The remote server 830 can also host application services directly, or over the internet 820.

FIG. 8B shows one embodiment of a communication environment 850 operating via the communication network 800 for managing smart implant products, services and applications. A smart implant for example can identify alignment, joint movement, bone density, load forces and temperature data and the other parameters of interest herein previously described. This information can be conveyed via wireless services, for example, over a telecommunication network to event service providers. The event services can include orthopedic implant and patient event services for time critical, secure, and reliable messaging and reporting. This information is related to monitoring services responsible for medical reporting, patient/doctor and consulting offices, and research services, including medical device and pharmaceutical companies.

Figure 9:
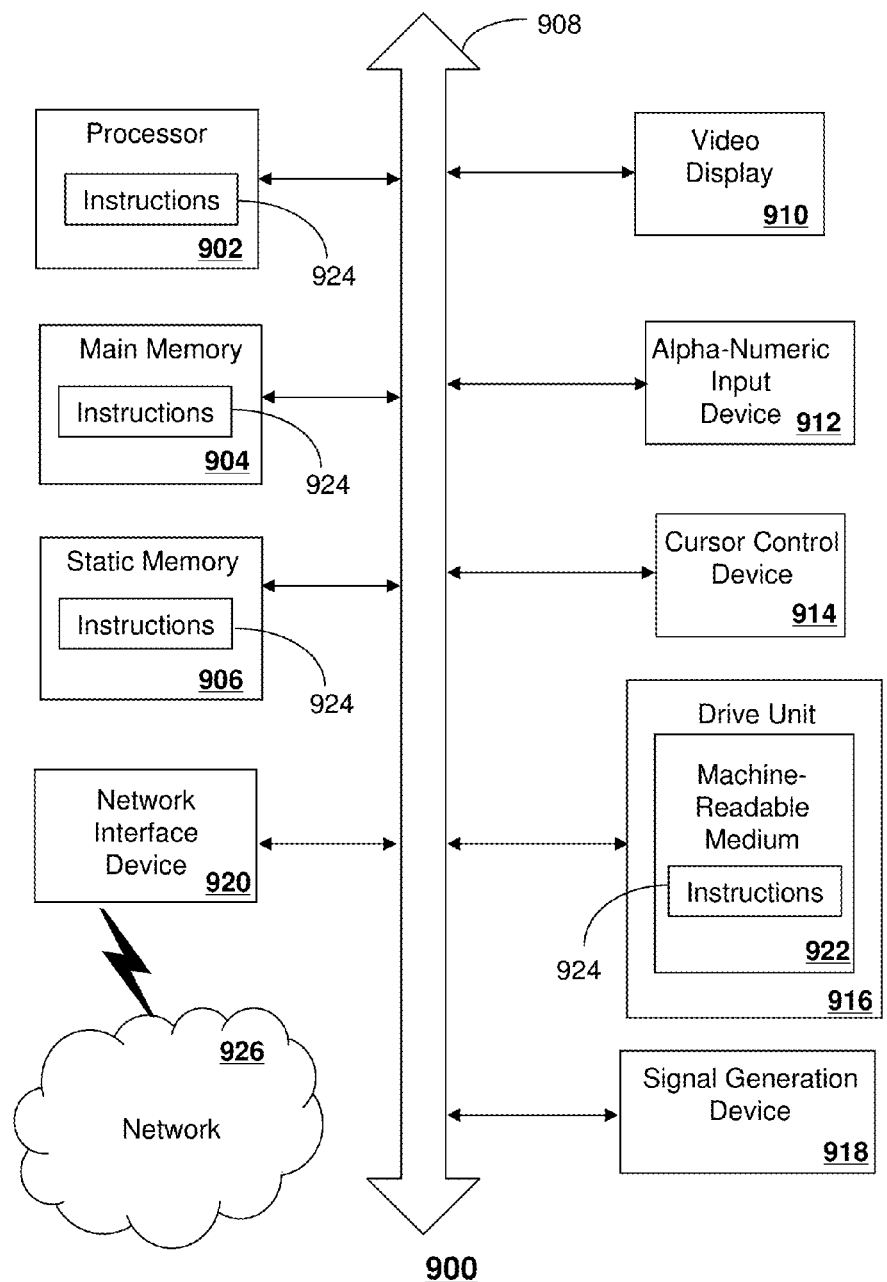
FIG. 9 depicts an exemplary diagrammatic representation of a machine in the form of a computer system within which a set of instructions, when executed, may cause the machine to perform any one or more of the methodologies disclosed herein.

FIG. 9 depicts an exemplary diagrammatic representation of a machine in the form of a computer system 900 within which a set of instructions, when executed, may cause the machine to perform any one or more of the methodologies discussed above. In some embodiments, the machine operates as a standalone device within the communication system 800 of FIG. 8A. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

The computer system 900 may include a processor 902 (e.g., a central processing unit (CPU), a graphics processing unit (GPU, or both), a main memory 904 and a static memory 906, which communicate with each other via a bus 908. The computer system 900 may further include a video display unit 910 (e.g., a liquid crystal display (LCD), a flat panel, a solid state display, or a cathode ray tube (CRT)). The computer system 900 may include an input device 912 (e.g., a keyboard), a cursor control device 914 (e.g., a mouse), a disk drive unit 916, a signal generation device 918 (e.g., a speaker or remote control) and a network interface device 920.

The disk drive unit 916 may include a machine-readable medium 922 on which is stored one or more sets of instructions (e.g., software 924) embodying any one or more of the methodologies or functions described herein, including those methods illustrated above. The instructions 924 may also reside, completely or at least partially, within the main memory 904, the static memory 906, and/or within the processor 902 during execution thereof by the computer system 900. The main memory 904 and the processor 902 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 924, or that which receives and executes instructions 924 from a propagated signal so that a device connected to a network environment 926 can send or receive voice, video or data, and to communicate over the network 926 using the instructions 924. The instructions 924 may further be transmitted or received over a network 926 via the network interface device 920.

While the machine-readable medium 922 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

These are but a few examples of embodiments and modifications that can be applied to the present disclosure without departing from the scope of the claims stated below. Accordingly, the reader is directed to the claims section for a fuller understanding of the breadth and scope of the present disclosure.

Where applicable, the present embodiments of the invention can be realized in hardware, software or a combination of hardware and software. Any kind of computer system or other apparatus adapted for carrying out the methods described herein are suitable. A typical combination of hardware and software can be a mobile communications device with a computer program that, when being loaded and executed, can control the mobile communications device such that it carries out the methods described herein. Portions of the present method and system may also be embedded in a computer program product, which comprises all the features enabling the implementation of the methods described herein and which when loaded in a computer system, is able to carry out these methods.

While the preferred embodiments of the invention have been illustrated and described, it will be clear that the embodiments of the invention are not so limited. Numerous modifications, changes, variations, substitutions and equivalents will occur to those skilled in the art without departing from the spirit and scope of the present embodiments of the invention as defined by the appended claims.

What is claimed is:

1. A surgical orthopedic alignment system comprising:
   a receiver, where the receiver includes a first transducer that is configured to receive or emit an ultrasonic signal, and where the receiver is configured to contact a portion of a muscular skeletal system;
   a wand, where the wand includes a second transducer that is configured to emit or receive the ultrasonic signal, where the wand is configured to be moveable to a point on at least one of the muscular skeletal system or a device; and
   a processor, where the processor is configured to use the time of flight of the ultrasonic signal between the wand and the receiver to determine positional location of the wand with respect to the receiver, where the positional location of the wand with respect to the receiver is used to determine alignment of the portion of the muscular skeletal system with respect to the point, where the determination of alignment occurs within a sterile field of an operating room, where the receiver further includes a controller operatively communicatively coupled to the first transducer, and where the receiver further includes an accelerometer.

2. The orthopedic alignment system of claim 1 further including an attachment mechanism, where the attachment mechanism attaches the receiver to the portion of the muscular-skeletal system.

3. The orthopedic alignment system of claim 1 where the wand comprises:
   a plurality of ultrasonic transducers; and
   a tip, where the tip is configured to be placed in contact with the point of interest.

4. The orthopedic alignment system of claim 3 where the wand is held by hand and is configured to be moved from one point of interest to another point of interest registering each point of interest.

5. The orthopedic alignment system of claim 3 where the wand is coupled to a fixture in a predetermined stationary position within the sterile field after points of interests have been registered.

6. The orthopedic alignment system of claim 1 where the wand and receiver are disposable.

7. The orthopedic alignment system of claim 1 where a graphical user interface resides on at least one of the wand and the receiver.

8. The alignment system of claim 7, where the system is configured to register multiple points of interest when the muscular skeletal system is moved.

9. The alignment system of claim 8, where the processor is configured to use data saved during the registration of the multiple points of interest to compute the alignment of the orthopedic system with respect to a mechanical axis of the orthopedic system.

10. The alignment system of claim 9, where the orthopedic system is a knee joint.

11. The alignment system of claim 9, where the orthopedic system is a hip joint.

12. The alignment system of claim 9, where the orthopedic system is a spinal column.

* * * * *